US010499859B2

(12) United States Patent
Iizuka et al.

(10) Patent No.: US 10,499,859 B2
(45) Date of Patent: Dec. 10, 2019

(54) IMAGE DISPLAY APPARATUS, IMAGE DISPLAY METHOD, AND STORAGE MEDIUM

(71) Applicant: CANON KABUSHIKI KAISHA, Tokyo (JP)

(72) Inventors: Yoshio Iizuka, Takatsuki (JP); Gakuto Aoyama, Kyoto (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 103 days.

(21) Appl. No.: 15/681,807

(22) Filed: Aug. 21, 2017

(65) Prior Publication Data

US 2018/0055461 A1 Mar. 1, 2018

(30) Foreign Application Priority Data

Aug. 31, 2016 (JP) ................. 2016-169608

(51) Int. Cl.
*A61B 6/03* (2006.01)
*A61B 5/00* (2006.01)
*A61B 6/00* (2006.01)

(52) U.S. Cl.
CPC ............ *A61B 6/035* (2013.01); *A61B 5/0033* (2013.01); *A61B 5/0035* (2013.01); *A61B 5/0073* (2013.01); *A61B 5/7425* (2013.01); *A61B 6/032* (2013.01); *A61B 6/463* (2013.01); *A61B 6/466* (2013.01); *A61B 6/467* (2013.01); *A61B 6/486* (2013.01); *A61B 6/5235* (2013.01)

(58) Field of Classification Search
CPC ... A61B 5/0033; A61B 5/0035; A61B 5/0073; A61B 5/7425; A61B 6/035; A61B 6/467
See application file for complete search history.

(56) References Cited

U.S. PATENT DOCUMENTS

| | | | |
|---|---|---|---|
| 9,898,839 B2* | 2/2018 | Kobayashi | A61B 6/502 |
| 2012/0321161 A1* | 12/2012 | Ishikawa | G06T 19/00 |
| | | | 382/131 |
| 2015/0052471 A1* | 2/2015 | Chen | A61B 6/025 |
| | | | 715/771 |
| 2015/0363907 A1* | 12/2015 | Satoh | G06T 7/30 |
| | | | 382/289 |
| 2016/0306936 A1* | 10/2016 | Mizobe | G06F 19/321 |

FOREIGN PATENT DOCUMENTS

JP          8-77329 A          3/1996

* cited by examiner

*Primary Examiner* — Marcus H Taningco
(74) *Attorney, Agent, or Firm* — Canon U.S.A., Inc. IP Division

(57) ABSTRACT

An image display apparatus includes a selection unit configured to select as a display image a second tomographic image in the case where a second acquisition unit successfully acquires the second tomographic image or in the case where a correspondence relationship between a first tomographic image and the second tomographic image satisfies a predetermined condition, or select a notification image in a case other than the above-described cases, and a display unit configured to display the first tomographic image and the display image selected by the selection unit in parallel or in a superimposed manner.

10 Claims, 8 Drawing Sheets

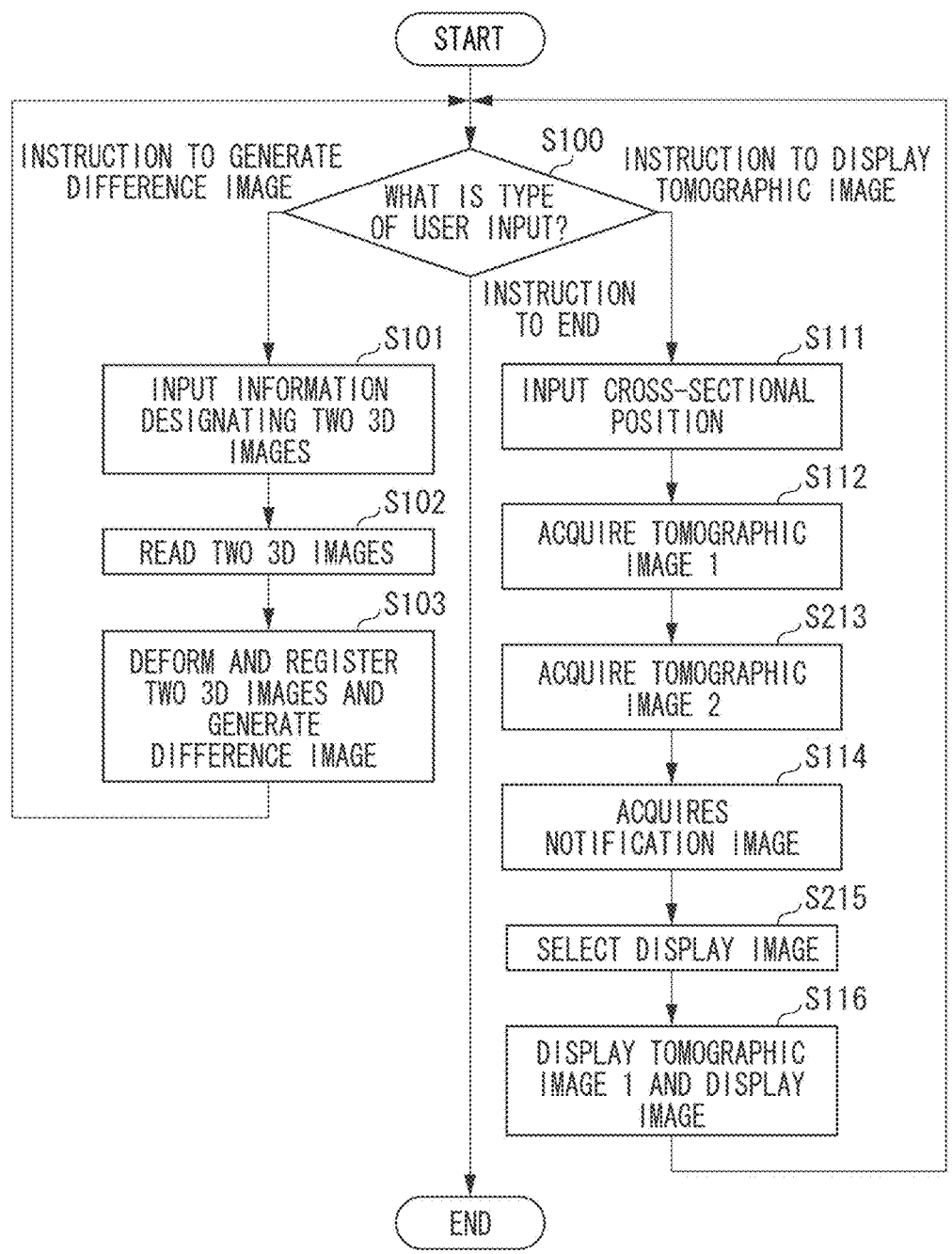

IMAGE DISPLAY APPARATUS, IMAGE DISPLAY METHOD, AND STORAGE MEDIUM

BACKGROUND

Field of the Disclosure

The present disclosure relates to an image display apparatus, an image display method, and a storage medium.

Description of the Related Art

In the medical field, doctors make diagnoses by observing medical images captured by various medical imaging apparatuses (modalities) such as X-ray computed tomographic (CT) apparatuses and magnetic resonance imaging (MRI) apparatuses. When images of the same patient are captured at different time points, the captured images are displayed next to each other, and doctors observe (i.e., perform comparative reading on) differences between the images. The comparative reading enables doctors to identify temporal changes in respective sites or lesion sites of the patient with ease and make an efficient, high-quality diagnosis.

In order to facilitate comparisons between two images, it is useful to register anatomically-corresponding positions between the images. Known techniques for the registration include linear registration techniques such as affine transformation and non-linear registration techniques such as free form deformation (FFD). Two images are registered using such an image registration technique, and then differences between pixel values of corresponding pixels are calculated to generate a difference image. The generated difference image is generally an image in which only a portion with a temporal change is highlighted, so doctors can identify a temporal change in a lesion site with ease.

Conventional image display apparatuses display three images next to each other that are a previously-captured image (previous image), a currently-captured image (current image), and a difference image generated from the previous image and the current image. Alternatively, a color difference image which is colored according to respective pixel values of the difference image is generated and superimposed on the current image. Japanese Patent Application Laid-Open No. 8-77329 discusses a technique for adding a time-series processed image (difference image) to a time-series image (original image) on which gradation processing is performed, and displaying the added image. This technique is discussed as a technique that can visibly display temporal changes of objects.

When previous and current images are both three-dimensional images each including a plurality of tomographic images, an image display apparatus displays a tomographic image of a cross-sectional position designated by the user. However, since the imaging range with respect to a patient differs in each image capturing, captured images do not always include the same site of the patient. Specifically, there can be a case in which no corresponding tomographic image exists between the previous and current images. That is to say, there can be a cross-sectional position for which a tomographic image exists with respect to only one of the current and previous images (while no tomographic image exists with respect to the other one), and for such a cross-sectional position, it is not possible to generate a difference image. When a tomographic image of such a cross-sectional position of the current image (or previous image) is displayed on a screen, since there is no corresponding tomographic image of the difference image, nothing is displayed on a difference image display area of the screen. Alternatively, some image display apparatuses display a tomographic image of the difference image that is located at the closest position to a cross-sectional position of a current image (or previous image).

SUMMARY

In the case where nothing is displayed on a difference image display area on a screen, a user can fail to notice that no tomographic image of a difference image exists and misunderstand that every pixel value of the tomographic image of the difference image is zero, i.e., the user can misunderstand that there is no temporal change. In the case where a color difference image is superimposed on a current image. The user is highly likely to mistakenly believe that no color pixel value is superimposed because there is no temporal change. Further, the same issue can occur in the case where current and difference images are displayed next to each other. The user is also highly likely to misunderstand that there is no temporal change if a display method used in the case where there is no tomographic image of the difference image is not different from a display method used in the case where there is a tomographic image of the difference image in which every pixel value is zero. In the case where there is a temporal change, such as the appearance of a lesion site, in a cross-sectional position, the user referring to the display of the difference image can misunderstand that there is no temporal change, and thereby can overlook the appearance of the lesion site.

In the case where a tomographic image of a difference image that is located at the closest position to a cross-sectional position of a current image is displayed, a different problem arises. In other words, the tomographic image of the difference image at the closest position may include a pixel value that is not zero, although there is no temporal change in the cross-sectional position of the current image. In such a case, it can cause the user to misunderstand that there is a temporal change.

Thus, display designs need to be arranged such that the user is not likely to be misled about the existence/nonexistence of a temporal change when there is no tomographic image of a difference image with respect to a cross-sectional position that corresponds to a tomographic image of a current image.

The present invention is directed to an image display apparatus and an image display method capable of clearly specifying the nonexistence of a tomographic image to the user in the case where there is no tomographic image of a three-dimensional difference image at a cross-sectional position that corresponds to a tomographic image of a three-dimensional image. The present invention is directed to not only the foregoing but also providing an effect that can be produced by each configuration described in an exemplary embodiment to be described below and is not produced by conventional techniques is also positioned as another aim.

According to an aspect of the present invention, an image display apparatus includes a first acquisition unit configured to acquire a first tomographic image from a first three-dimensional image including a plurality of tomographic images, a second acquisition unit configured to acquire a second tomographic image at a cross-sectional position corresponding to the first tomographic image from a processed image obtained by performing image processing on the first three-dimensional image and a second three-dimensional image, a third acquisition unit configured to acquire a notification image for notifying that the second acquisition unit is unsuccessful in acquiring the second tomographic image or that a correspondence relationship between the first tomographic image and the second tomographic image does not satisfy a predetermined condition, a selection unit configured to select the second tomographic image as a display image in a case where the second acquisition unit successfully acquires the second tomographic image or in a case where the correspondence relationship between the second tomographic image and the second tomographic image satisfies the predetermined condition, or select the notification image as a display image in a case where the second acquisition unit unsuccessfully acquires the second tomographic image or in a case where the correspondence relationship does not satisfy the predetermined condition, and a display unit configured to display the first tomographic image and the display image selected by the selection unit in parallel or in a superimposed manner.

Further features of the present invention will become apparent from the following description of exemplary embodiments with reference to the attached drawings.

BRIEF DESCRIPTION OF THE DRAWINGS

FIG. 8 is a flow chart illustrating a process according to a second exemplary embodiment of the present invention.

DESCRIPTION OF THE EMBODIMENTS

Image display apparatuses according to various exemplary embodiments of the present invention will be described below with reference to the drawings. It should be noted, however, that the scope of the invention is not limited to the illustrated examples.

The following describes a first exemplary embodiment. An image display apparatus according to the first exemplary embodiment displays tomographic images of a first three-dimensional image and a processed three-dimensional image either next to each other or with one of the tomographic images superimposed on the other such that the existence/nonexistence of the tomographic image of the processed three-dimensional image is recognizable with ease.

In the following description, a current image of a patient is used as an example of the first three-dimensional image and a previous image of the same patient as an example of a second three-dimensional image. However, the first and second three-dimensional images are not limited to the above-described examples. For example, the first and second three-dimensional images can be arbitrary three-dimensional images captured at different time points or three-dimensional images generated as a statistically-standard model (standard model). Further, for example, the first and second three-dimensional images can be three-dimensional images of different patients, three-dimensional images captured by different modalities, or three-dimensional images acquired by mirror-reversing one three-dimensional image. In other words, the present exemplary embodiment is applicable to any three-dimensional image.

In the following description, a difference image is used as an example of a processed image acquired by performing image processing on the first and second three-dimensional images. The difference image is generated by, for example, performing registration between the first and second three-dimensional images using a publicly-known non-linear registration technique and then calculating difference values between corresponding pixels. However, the image processing is not limited thereto. Other examples of the image processing include filtering processing such as smoothing processing or edge enhancement processing on an entire image, region extraction processing for extracting a region of interest such as an abnormal shadow region or specific organ region, and feature amount extraction processing for extracting a feature amount of an image. In other words, the present exemplary embodiment is applicable to a processed image acquired by any image processing.

The exemplary embodiments described below are mere illustrations of a method of processing performed by the image display apparatus.

Figure 1:
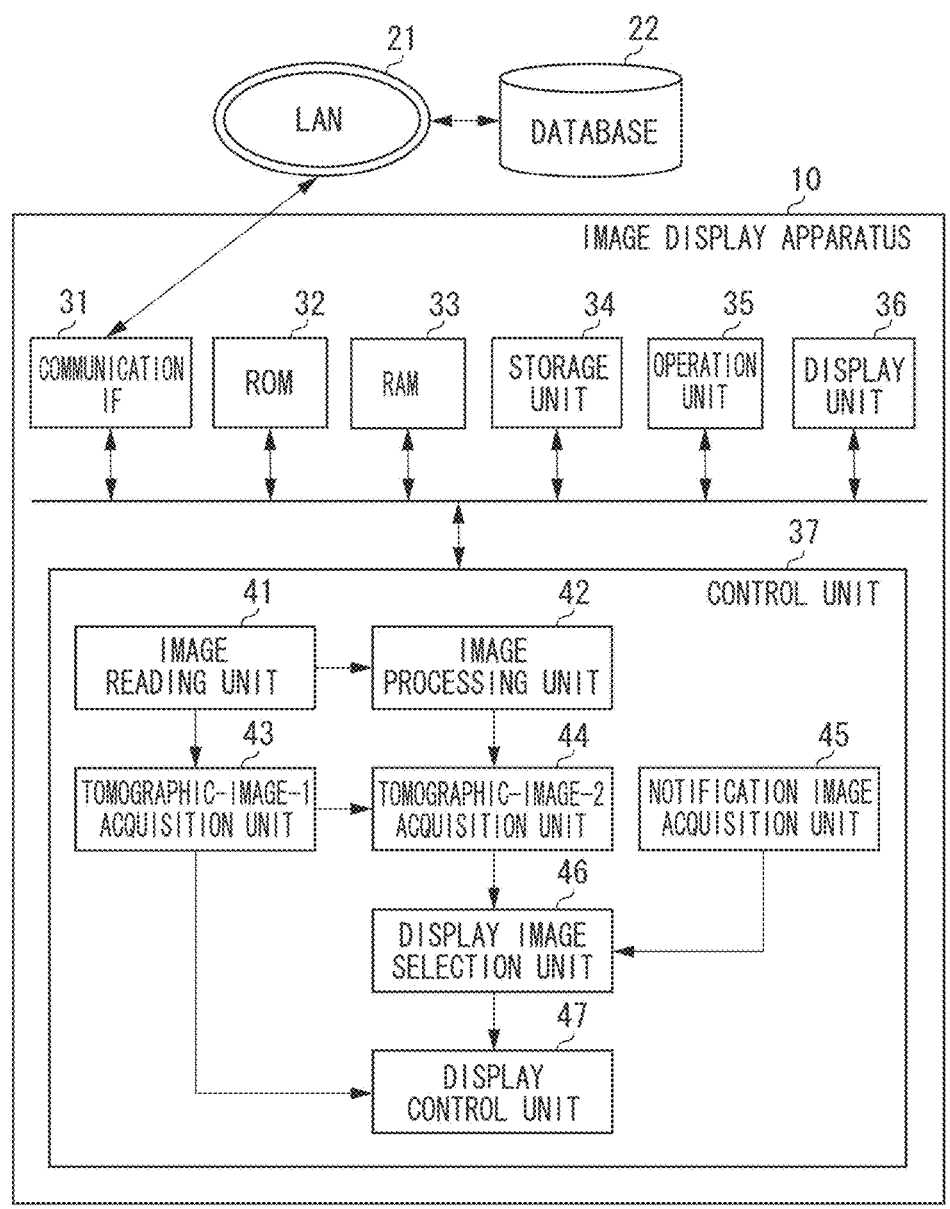
FIG. 1 illustrates an entire configuration of an image display system including an image display apparatus according to a first exemplary embodiment of the present invention.

FIG. 1 illustrates the entire configuration of an image display system including the image display apparatus according to the first exemplary embodiment.

The image display system includes an image display apparatus 10 and a database 22, which are connected to communicate with each other via a communication unit 21. In the present exemplary embodiment, the communication unit 21 includes a local area network (LAN).

The database 22 stores and manages data such as medical images. The image display apparatus 10 acquires via the communication unit (hereinafter, "LAN") 21 the medical images managed by the database 22.

The image display apparatus 10 has a functional configuration including a communication interface (IF) 31, a read-only memory (ROM) 32, a random access memory (RAM) 33, a storage unit 34, an operation unit 35, a display unit 36, and a control unit 37.

The communication IF 31 is realized by a LAN card or other hardware and enables communication between an external device (e.g., database 22) and the image display apparatus 10. The ROM 32 is realized by a non-volatile memory or the like and stores various programs, etc. The RAM 33 is realized by a volatile memory and temporarily stores various types of information. The storage unit 34 is realized by a hard disk drive (HDD) and stores various types of information. The operation unit 35 is realized by a keyboard or mouse and inputs user instructions to the image display apparatus 10. The display unit 36 is realized by a display and displays various types of information to the user. The control unit 37 is realized by a central processing unit (CPU) and comprehensively controls processing performed at the image display apparatus 10.

The control unit 37 has a functional configuration including an image reading unit 41, an image processing unit 42, a tomographic-image-1 acquisition unit 43, a tomographic-image-2 acquisition unit 44, a notification image acquisition unit 45, a display image selection unit 46, and a display control unit 47. The functions of the respective units included in the control unit 37 will be described below together with a description of a flow chart illustrated in FIG. 2.

Figure 2:
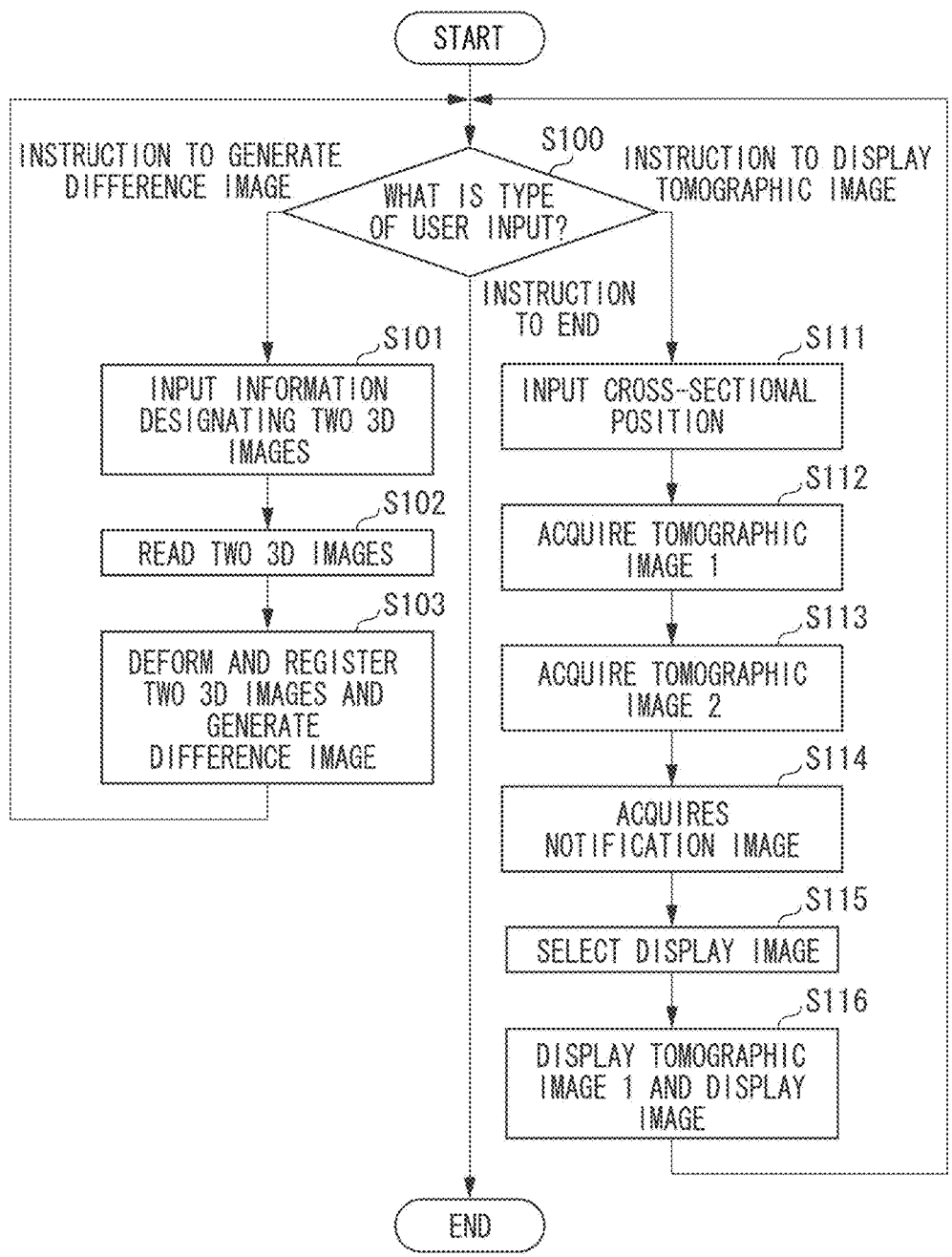
FIG. 2 is a flow chart illustrating a process according to the first exemplary embodiment of the present invention.

FIG. 2 is a flow chart illustrating a process according to the first exemplary embodiment of the present invention which is controlled by the control unit 37 of the image display apparatus 10.

In step S100 in FIG. 2, the control unit 37 determines next processing to be executed according to the type of user input which is input from the operation unit 35. If the user input is an instruction to generate a difference image (INSTRUCTION TO GENERATE DIFFERENCE IMAGE in step S100), the processing proceeds to step S101. If the user input is an instruction to display a tomographic image (INSTRUCTION TO DISPLAY TOMOGRAPHIC IMAGE in step S100), the processing proceeds to step S111. If the user input is an instruction to end the processing (INSTRUCTION TO END in step S100), the process according to the present exemplary embodiment is ended. While there are many other types of user input, description thereof is omitted to facilitate understanding.

The following describes a process performed in the case where the user input is an instruction to generate a difference image.

In step S101, the control unit 37 accepts from the operation unit 35 information designating a first three-dimensional image and information designating a second three-dimensional image, as necessary information for generating a difference image. In the following description, an example in which the first three-dimensional image is a current image and the second three-dimensional image is a previous image will be described.

In step S102, the image reading unit 41 reads current image data and previous image data from the database 22 via the communication IF 31 and the LAN 21 based on the information input in step S101, and stores the current image data and the previous image data in the storage unit 34.

In step S103, the image processing unit 42 reads the current image data and the previous image data stored in the storage unit 34, performs registration between the images using a publicly-known deformation and registration technique, and then generates a difference image. The generated difference image is stored in the storage unit 34, and then the processing returns to step S100.

In the above-described deformation and registration between images, only one of the images (normally, previous image) is deformed with respect to the other one of the images (normally, current image) to register the images. Then, pixel values of the deformed image are respectively subtracted from pixel values of the other image to generate a difference image.

Since the imaging range (body site) or posture of the patient can be changed in each image capturing, and since the arrangement of pixels is changed by the image deformation, in general there may be a plurality of pixels that does not correspond between the current image and the previous image. A difference image can be generated only if there are corresponding pixels between the current image and the previous image, i.e., a difference image can be generated only with respect to an overlapping portion of imaging ranges, so in general, the number of tomographic images included in the difference image is smaller than those of the current image and the previous image. For example, in the case where the current image includes 500 tomographic images and the previous image includes 400 tomographic images, if only 250 of the corresponding tomographic images between the current image and the previous image, the number of tomographic images of the difference image is 250. That is to say, the difference image may include no tomographic image of a cross-sectional position corresponding to a tomographic image of the current image or the previous image.

Figure 3:
FIG. 3 illustrates a first example of the correspondence relationship between tomographic images of a plurality of three-dimensional images.

The following describes a first example of the correspondence relationship between tomographic images of a plurality of three-dimensional images, with reference to FIG. 3. In FIG. 3, positions P1 to P9 are cross-sectional positions based on cross-sectional positions of the current image. In the case where the current image includes tomographic images of the cross-sectional positions P1 to P7 and the previous image includes tomographic images of the cross-sectional positions P4 to P9, since the image registration can be performed only with respect to the cross-sectional positions at which the previous image and the current image overlap, a deformed previous image and a difference image can be generated only with respect to the cross-sectional positions P4 to P7. While the cross-sectional positions P4 to P9 are described above as the cross-sectional positions of the previous image to facilitate understanding, the cross-sectional positions of the previous image and the current image or intervals therebetween do not have to be the same. Further, the normal directions of the cross-sectional images of the previous image and the current image are not always the same with respect to the patient body. For this reason, the image deformation and registration are performed. Deformed and registered tomographic images of the previous image are generated to align with the cross-sectional positions based on the cross-sectional positions of the current image, so tomographic images of the difference image are also generated to align with the same cross-sectional positions.

The following describes a process performed in the case where the user input is an instruction to display a tomographic image.

In step S111, the control unit 37 inputs from the operation unit 35 information (cross-sectional position designation information) for selecting a tomographic image to be displayed on the display unit 36 from the tomographic images of the current image. If a tomographic image is already displayed on the display unit 36, the user can give an instruction to display a tomographic image of the next or previous cross-sectional position. The instruction to display a tomographic image of the next or previous cross-sectional position includes both the instruction to display a tomographic image and the cross-sectional position designation information, so the user only needs to give one instruction. That is to say, the instruction to display a tomographic image in step S100 and the cross-sectional position designation information in step S111 are simultaneously input by the one instruction.

In step S112, the tomographic-image-1 acquisition unit 43 acquires a tomographic image (tomographic image 1) of the current image that is read by the image reading unit 41 and stored in the storage unit 34, and temporarily stores the acquired tomographic image in the RAM 33. At this time, the tomographic image of the cross-sectional position acquired in step S111 is acquired as the tomographic image 1. The tomographic image 1 is used in step S116 described below.

In step S113, the tomographic-image-2 acquisition unit 44 acquires a tomographic image (tomographic image 2) of the difference image that is generated by the image processing unit 42 and stored in the storage unit 34. At this time, the tomographic image of the cross-sectional position acquired in step S111 is acquired as the tomographic image 2. However, depending on the cross-sectional position, the difference image includes no tomographic image, so there can be a case where no tomographic image 2 can be acquired (and temporarily stored in the RAM 33). For example, in the example illustrated in FIG. 3, it is possible to acquire a tomographic image 1 but impossible to acquire tomographic images 2 with respect to the cross-sectional positions P1 to P3. Meanwhile, it is possible to acquire both tomographic images 1 and 2 with respect to the cross-sectional positions P4 to P7. The tomographic image 2 is used in step S115 described below.

In step S114, the notification image acquisition unit 45 acquires a notification image. Examples of the notification image will be described below. In the case where the same image is always used as a notification image, the notification image is stored in advance in the storage unit 34, and at the time of the execution of step S114, the notification image is read from the storage unit 34 and temporarily stored in the RAM 33. On the other hand, in the case where a notification image is changed by a predetermined method described below, a notification image is generated or changed and temporarily stored in the RAM at the time of the execution of step S114. The processing of step S114 may be omitted in the case where the tomographic image 2 is acquired in step S113.

In step S115, the display image selection unit 46 selects the tomographic image 2 as a display image in the case where the tomographic image 2 is acquired in step S113, or selects the notification image as a display image in the case where no tomographic image 2 is acquired in step S113. In the case where both the notification image and the tomographic image 2 are acquired, the both images are temporarily stored in the RAM 33, so the display image selection unit 46 selects a display image by selecting a storage location in the RAM 33 in which one of the notification image and the tomographic image 2 is temporarily stored.

In step S116, the display control unit 47 displays on the display unit 36 the tomographic image 1 acquired and temporarily stored in the RAM 33 in step S112 and the display image selected in step S115 in parallel or in a superimposed manner. Further, at this time, the display control unit 47 can also display on the display unit 36 a tomographic image (tomographic image 3) of the previous image that corresponds to the cross-sectional position of the tomographic image 1. At this time, all the tomographic images 1, 2, and 3 can be displayed next to each other, or the tomographic images 1 and 3 can be displayed next to each other with the tomographic image 2 superimposed on the tomographic image 1. Any other display method can also be employed.

Each pixel value of the difference image is either a positive value or negative value, so at the time of displaying the tomographic image of the difference image on the display unit 36, the display control unit 47 adds a predetermined value to every pixel value to change the pixel values to positive values and then displays the tomographic image. Alternatively, the display control unit 47 can acquire the absolute values of all pixel values to change the pixel values to positive values and then display the tomographic image. Alternatively, predetermined colors can be assigned according to the ranges of respective pixel values to display the images in color. Any publicly-known method can be used to display the difference image.

While the tomographic image of the current image is described as the tomographic image 1 in the above-described exemplary embodiment, a tomographic image of the previous image can be the tomographic image 1. In this case, the cross-sectional position of the previous image is used as a reference, so the current image is deformed and registered with respect to the previous image and then a difference image is generated.

Figure 4:
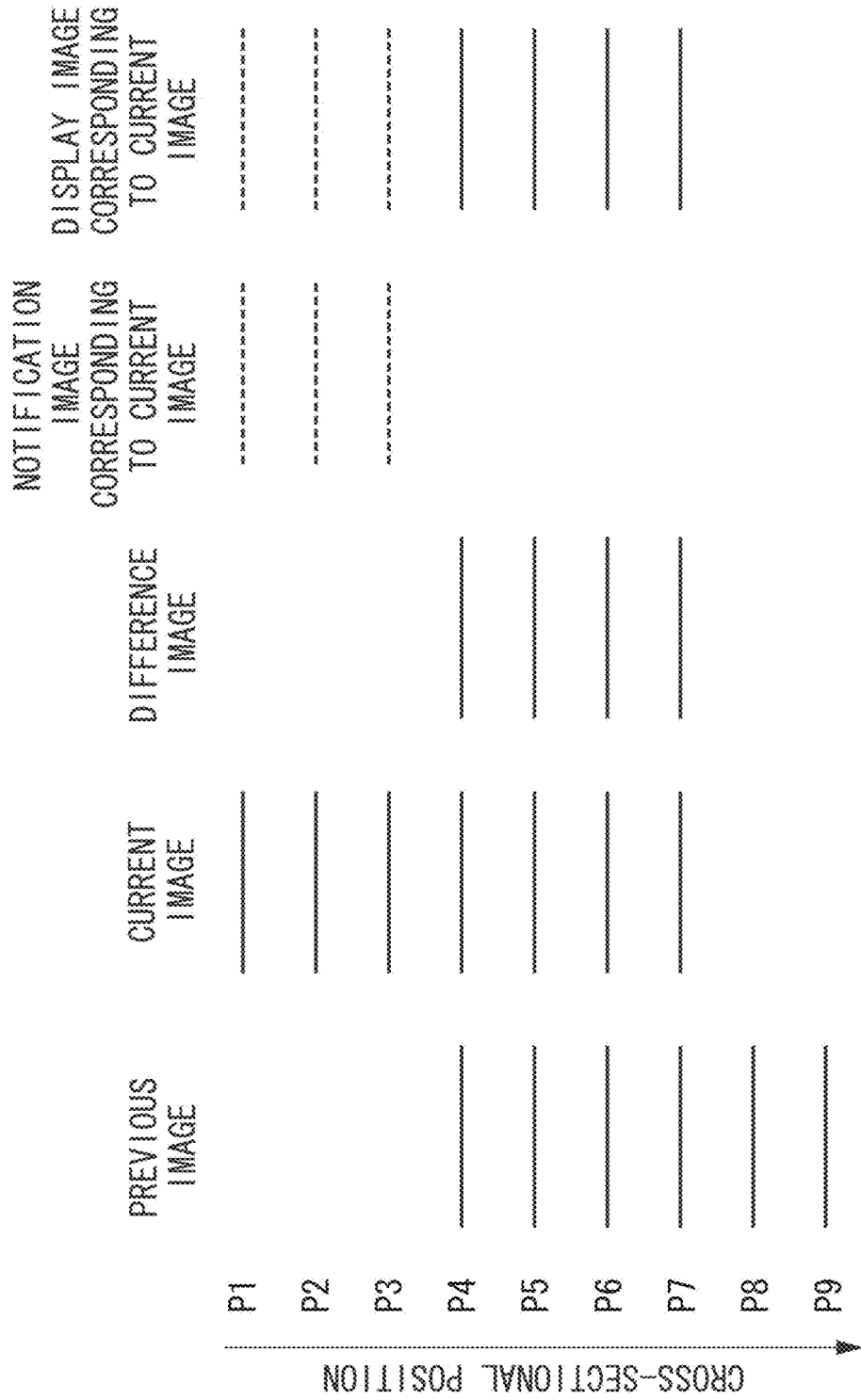
FIG. 4 illustrates a second example of the correspondence relationship between tomographic images of a plurality of three-dimensional images.
Figure 5:
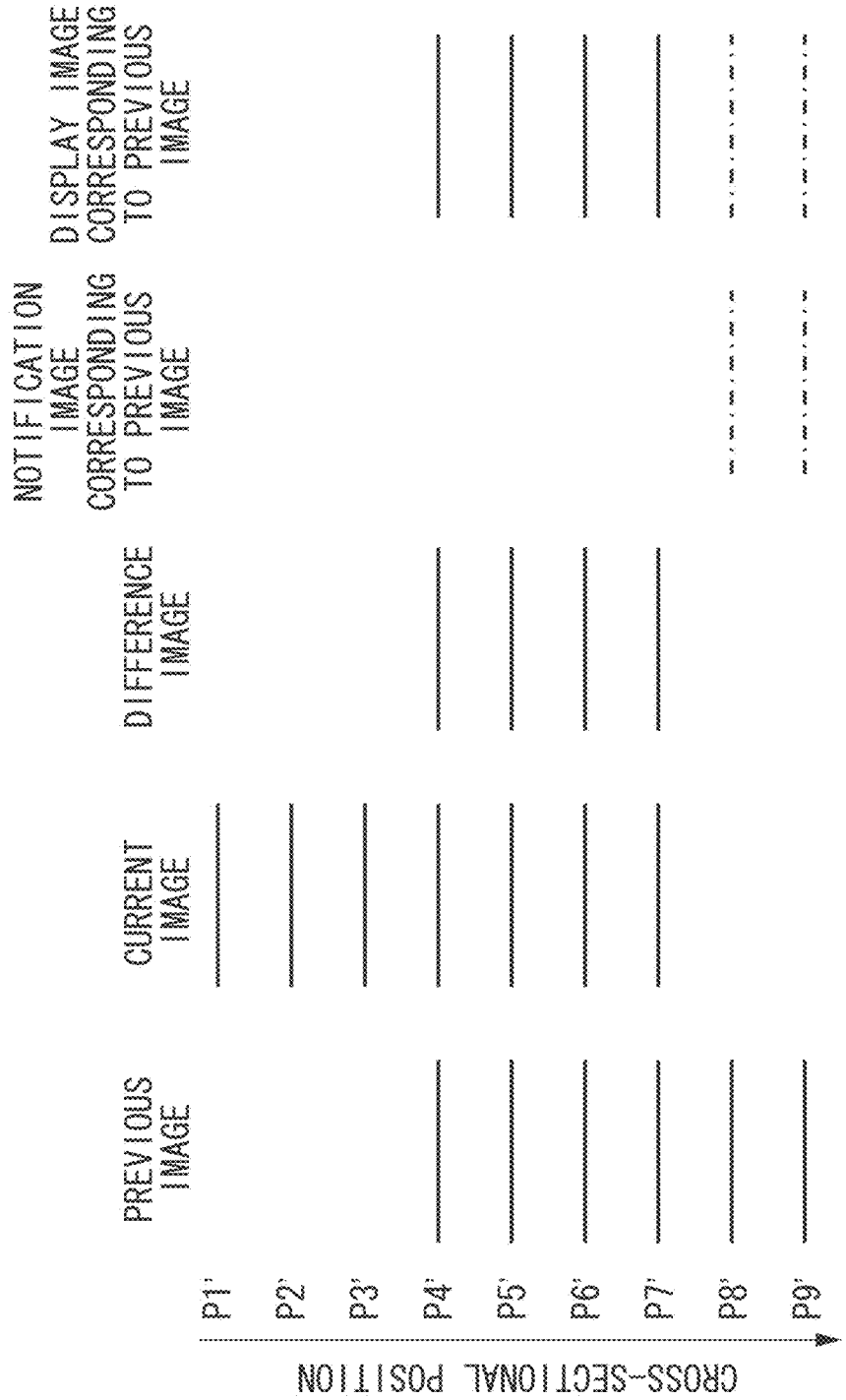
FIG. 5 illustrates a third example of the correspondence relationship between tomographic images of a plurality of three-dimensional images.

The following describes second and third examples of the correspondence relationship between tomographic images of a plurality of three-dimensional images, with reference to FIGS. 4 and 5.

FIG. 4 illustrates an example of cross-sectional positions of tomographic images of respective three-dimensional images in the case where the previous image is deformed and registered with respect to the current image and then a difference image is generated. In the case where the current image includes tomographic images at the cross-sectional positions P1 to P7 and tomographic images of the difference image are generated with respect to the cross-sectional positions P4 to P7, a notification image is output with respect to the cross-sectional positions P1 to P3. As a result, the notification image is selected with respect to the cross-sectional positions P1 to P3 as a display image, and the tomographic images of the difference image are selected with respect to the cross-sectional positions P4 to P7 as a display image.

FIG. 5 illustrates an example of cross-sectional positions of tomographic images of respective three-dimensional images in the case where the current image is deformed and registered with respect to the previous image and then a difference image is generated. In the case where the previous image includes tomographic images at cross-sectional positions P4' to P9' and tomographic images of the difference image are generated with respect to the cross-sectional positions P4' to P7', a notification image is output with respect to the cross-sectional positions P8' to P9'. As a result, the tomographic images of the difference image are selected with respect to the cross-sectional positions P4' to P7' as a display image, and the notification image is selected with respect to the cross-sectional positions P8' to P9' as a display image.

The following describes examples of screen displays of the tomographic image 1, the display image, and the superimposed image with the display image superimposed on the tomographic image 1 with respect to two cross-sectional positions, with reference to FIGS. 6A, 6B, 6C, 7A, 7B, and 7C.

Figure 6A:
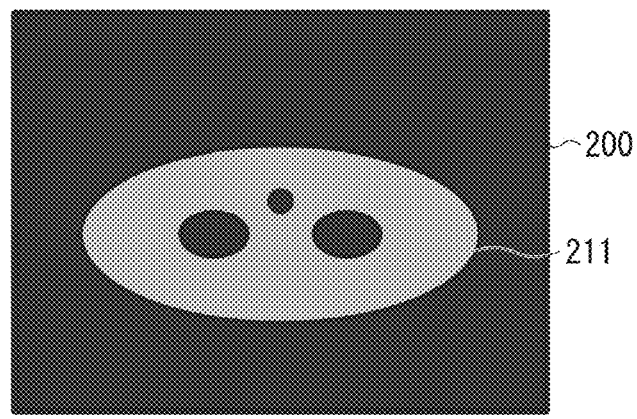
FIGS. 6A, 6B and 6C illustrate first screen display examples of a tomographic image, a display image, and a superimposed image of the tomographic image and the display image.
Figure 6B:
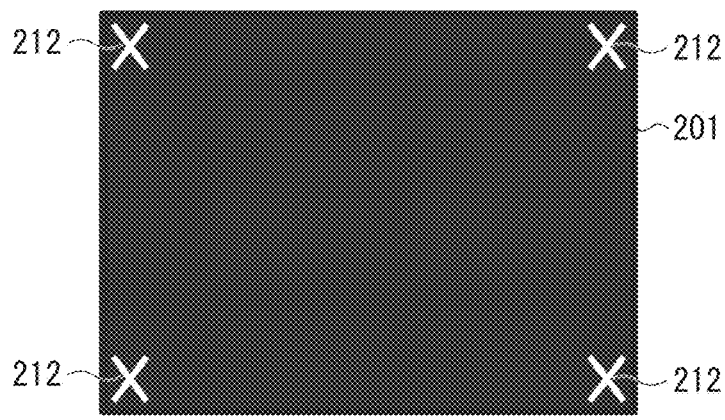
Figure 6C:
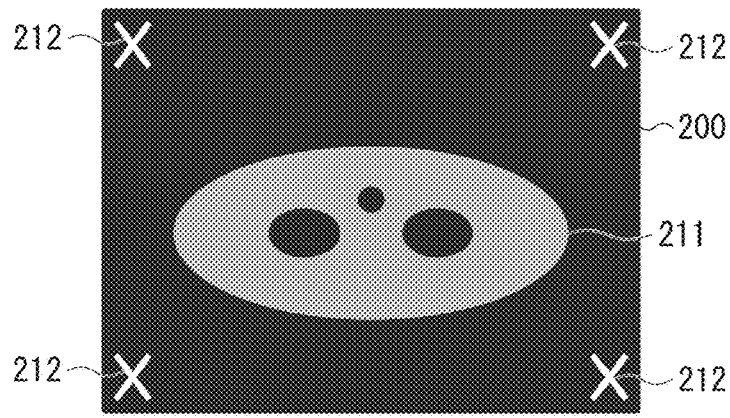

FIGS. 6A to 6C illustrate examples of screen displays of respective tomographic images with respect to the cross-sectional position P2 specified in FIG. 4. FIG. 6A illustrates an example of the screen display of the tomographic image 1. In FIG. 6A, the tomographic image 1 of the cross-sectional position P2 including an object (a portion of a body site of the patient) 211 is displayed in an image display area 200. FIG. 6B illustrates an example of the screen display of the display image (notification image). In FIG. 6B, the notification image including information 212 indicating that no difference image exists is displayed as a display image in an image display area 201. In the example illustrated in FIG. 6B, the notification image is an image with the mark "x" displayed at each of the four corners of the image display area 201, and every portion (pixel position) other than the portions with the mark "x" has a transparent pixel value. FIG. 6C illustrates an example of the screen display of the superimposed image with the display image (notification image) of FIG. 6B superimposed on the tomographic image 1 of FIG. 6A. In the case where the tomographic image 1 and the display image are to be displayed next to each other, the image display areas 200 and 201 are displayed next to each other on the display unit 36. In the notification image in the case where the tomographic image 1 and the display image are displayed next to each other, each portion (pixel position) other than the portions with the mark "x" has a predetermined pixel value (e.g., value of zero).

Figure 7A:
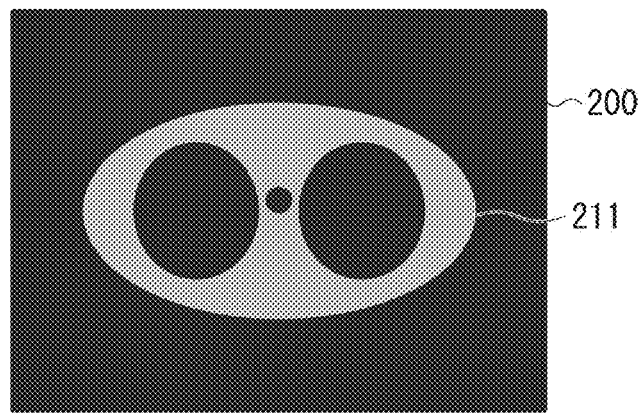
FIGS. 7A, 7B and 7C illustrate second screen display examples of a tomographic image, a display image, and a superimposed image of the tomographic image and the display image.
Figure 7B:
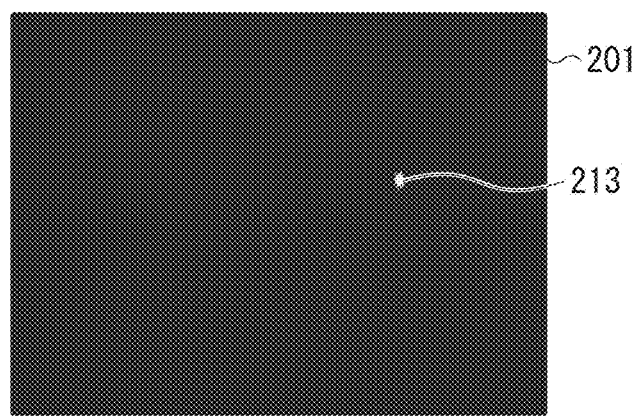
Figure 7C:
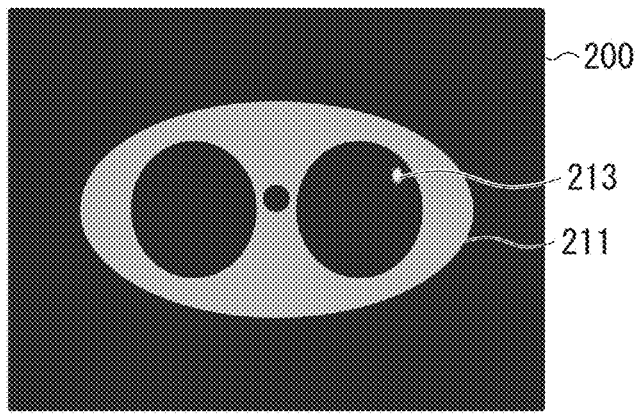

FIGS. 7A to 7C illustrate examples of screen displays of respective tomographic images with respect to the cross-sectional position P5 specified in FIG. 4. FIG. 7A illustrates an example of the screen display of the tomographic image 1. In FIG. 7A, the tomographic image 1 of the cross-sectional position P5 including the object 211 is displayed on the image display area 200. FIG. 7B illustrates an example of the screen display of the display image (tomographic image 2). In FIG. 7B, the tomographic image 2 of the cross-sectional position P5 including a temporally-changed portion 213 is displayed as a display image in the image display area 201. In the example illustrated in FIG. 7B, there is the temporally-changed portion (portion with a difference value other than zero) 213 located slightly rightward from a center of the tomographic image 2, and every portion other than the temporally-changed portion 213 has a difference value of zero. FIG. 7C illustrates an example of the screen display of the superimposed image with the display image (tomographic image 2) of FIG. 7B superimposed on the tomographic image 1 of FIG. 7A.

From a comparison between FIGS. 6C and 7C, it can be understood that the notification image indicating that no tomographic image of the difference image exists is displayed with respect to the cross-sectional position for which no difference image is generated, so the user can recognize the nonexistence at once. Thus, in diagnostic imaging with reference to the difference image, the doctor user is not likely to overlook an appearance of a lesion site by misunderstanding that there is no temporal change in the cross-sectional position in which there is a temporal change but for which no difference image is generated. On the other hand, no notification image is displayed with respect to the cross-sectional position for which the difference image is generated and in which there is no temporal change. This enables the user to correctly understand the information indicating that there is no temporal change.

While the image with the mark "x" drawn in each of the four corners of the image is described as an example of the notification image in the example illustrated in FIG. 6B, the notification image can be any image that is easy to understand for the user. For example, the notification image can be an image in which the text "no difference image" or the like is embedded or an image which includes a predetermined region filled with a predetermined color (semitransparent color) or which is entirely filled with the predetermined color. Further, for example, the design (text, mark, graphic, color, transparency) of the notification image with respect to the current image can be different from the design of the notification image with respect to the previous image. Further, for example, the processing performed by the notification image acquisition unit 45 in step S114 can be changed as follows to change the design of the notification image either stepwise or continuously according to the cross-sectional position. Specifically, the notification image can be changed according to a difference between the cross-sectional position of the tomographic image 1 and the cross-sectional position of the closest tomographic image of the difference image to the cross-sectional position of the tomographic image 1 (distance between the cross-sectional positions). For example, the sizes of text, mark, and graphic drawn on the notification image can be changed by a predetermined ratio according to the distance, or the color and transparency can be changed by a predetermined ratio. Alternatively, a table which defines the correspondence relationship between values of the distance and designs of the notification image can be stored in advance in the storage unit 34, the design of the notification image is changed by referring to the table. In this way, the user can find out with ease the distance to a tomographic image for which the difference image exists. In the case where the tomographic image 2 (tomographic image of difference image) is displayed in color, it is suitable to clearly differentiate between colors for use in the tomographic image 2 and in the notification image so that the tomographic image 2 and the notification image are clearly distinguishable at a glance.

As to the processing according to the above-described first exemplary embodiment or modified example, at least a portion of components included in the control unit 37 can be realized as an independent apparatus, or as software configured to realize the functions of the components. Further, at least a part of the functions realized by the control unit 37 can be realized by cloud computing. Specifically, the image display apparatus 10 may be connected via the LAN 21 to a computation apparatus situated in a different location from the image display apparatus 10 to transmit and receive data so that the computation apparatus executes the above-described processing.

As described above, the image display apparatus according to the present exemplary embodiment is advantageous in that in the case where no tomographic image of a processed image (three-dimensional difference image, etc.) exists with respect to a cross-sectional position corresponding to a tomographic image of a first three-dimensional image, a notification of the nonexistence is provided (clearly specified) to the user. This produces an advantage that the doctor, i.e., user, is not likely to make a misdiagnosis by misunderstanding that there is no temporal change between the previous image and the current image.

The following describes a second exemplary embodiment. In the present exemplary embodiment, the apparatus configuration is similar to that illustrated in FIG. 1, so description of the apparatus configuration is omitted.

FIG. 8 illustrates a process according to the present exemplary embodiment. Many steps included in the process illustrated in FIG. 8 are similar to those illustrated in FIG. 2, and the same step numbers are given to similar steps in FIGS. 2 and 8. In the following description, steps 213 and S215, which are different from those in FIG. 2, will be described. Description of the other steps that are similar to those in FIG. 2 is omitted.

Depending on the method of generating a difference image, the cross-sectional positions and cross-sectional intervals may not be always the same between the current image and the difference image. For example, in the case where the cross-sectional positions and cross-sectional intervals differ between the current image and the previous image, if a difference image is generated according to the cross-sectional positions and cross-sectional intervals of the previous image, the cross-sectional positions and cross-sectional intervals are not the same between the current image and the difference image. For example, suppose that the cross-sectional position acquired in step S111 is located at a predetermined distance (e.g., 10 mm) from a reference position. At this time, in step S112, a tomographic image (tomographic image 1) of the current image at the cross-sectional position of 10 mm from the reference position is acquired. However, in step S113, there can be a case where no tomographic image (tomographic image 2) of the difference image exists at the cross-sectional position of 10 mm from the reference position but a corresponding tomographic image exists at a slightly different cross-sectional position (e.g., 12.5 mm).

In the following description, the absolute value of (Pa−Pb) is referred to as the distance between the tomographic images 1 and 2, where Pa is the cross-sectional position of the tomographic image 1 acquired in step S112, and Pg is the cross-sectional position of the tomographic image 2 acquired in step 113.

In step S213, the tomographic-image-2 acquisition unit 44 acquires the tomographic image (tomographic image 2) of the difference image that is generated by the image processing unit 42 and stored in the storage unit 34, and temporarily stores the acquired image in the RAM 33. At this time, the tomographic image at the closest position to the cross-sectional position acquired in step S111 is acquired as the tomographic image 2. At this time, the tomographic image 2 at the closest cross-sectional position is acquired, so the tomographic image of the difference image at the cross-sectional position P4 is acquired as the tomographic image 2 with respect to the cross-sectional positions P1 to P3 specified in FIG. 3.

In step S215, if the correspondence relationship between the tomographic images 1 and 2 satisfies a predetermined condition, the display image selection unit 46 selects the tomographic image 2 as a display image. On the other hand, if the correspondence relationship does not satisfy the predetermined condition, the notification image is selected as a display image. In the present exemplary embodiment, the predetermined condition is whether the distance between the tomographic images 1 and 2 is smaller than or equal to a predetermined threshold value. Specifically, if the distance between the tomographic images 1 and 2 is smaller than or equal to the predetermined threshold value, the display image selection unit 46 selects the tomographic image 2 as a display image, and if the distance between the tomographic images 1 and 2 is greater than the predetermined threshold value, the display image selection unit 46 selects the notification image as a display image.

By the above-described processing, the notification image can be displayed if the respective cross-sectional positions of the tomographic images 1 and 2 are different from each other and the distance between the tomographic images 1 and 2 is significantly different from a predetermined threshold value. In this way, if the difference between the tomographic images is significant, a notification of the significant difference can be provided to the user. The display image to be selected in the case where the condition is not satisfied can be a combined image of the tomographic image 2 and the notification image. Examples of an image that can be used as the combined image include an image with the notification image superimposed on the tomographic image 2.

Modified Example 1

First and second threshold values can be set as the threshold value for the distance between the tomographic images 1 and 2, and the display image selection can be performed based on the two threshold values. It should be noted, however, that the second threshold value is larger than the first threshold value.

For example, in step S215 described above, if the distance between the tomographic images 1 and 2 is smaller than or equal to the first threshold value (condition 1), the display image selection unit 46 selects the tomographic image 2 as a display image. On the other hand, if the distance is greater than the first threshold value but is smaller than or equal to the second threshold value (condition 2), the display image selection unit 46 selects the combined image (e.g., superimposed image) of the tomographic image 2 and the notification image as a display image. Further, if the distance is greater than the second threshold value (condition 3), the display image selection unit 46 selects the notification image as a display image.

In the case of the condition 2, the combining ratio used to generate the combined image of the tomographic image 2 and the notification image can be changed according to the distance between the tomographic images 1 and 2. Specifically, the combining processing can be performed such that the ratio of the notification image becomes higher as the distance becomes greater. Further, a combined image can be generated by combining the tomographic image 2 with the notification image, using a combining ratio such that the higher the ratio of the notification image becomes higher as the distance between the tomographic images 1 and 2 becomes greater, and the combined image thus generated can always be used as a display image. In other words, the combining ratio is set based on the difference between the tomographic images 1 and 2.

By the above-described processing, the difference image is displayed and the notification image warning the user that the cross-sectional position of the difference image is slightly different is superimposed in the case where the distance between the tomographic images 1 and 2 is slight. Further, in the case where the distance between the tomographic images 1 and 2 is significant, the notification image warning the user of the significant difference is displayed. In this way, the difference image and the notification image are simultaneously displayed in the case where the cross-sectional position is different to some extent but it is useful to refer to the difference image.

Modified Example 2

The predetermined condition used by the display image selection unit 46 to select a display image in step S215 can be a condition based on something other than the distance between the cross-sectional positions of the tomographic images 1 and 2.

In step S213 described above, the tomographic-image-2 acquisition unit 44 further calculates statistics of pixel values of the acquired tomographic image 2. Examples of the statistics include the total value of the absolute values, the mean value of the absolute values, variance value, and the maximum value of the absolute values.

In step S215 described above, the display image selection unit 46 further receives the statistic of pixel values of the acquired tomographic image 2 from the tomographic-image-2 acquisition unit 44 and determines whether the statistic is within a predetermined range. For example, in the case where the received statistic is the mean value of the absolute values of the pixel values, whether the received mean value is greater than a predetermined threshold value is determined. A greater statistic of the pixel values of the tomographic image 2 indicates a larger number of pixels with a large absolute value of a pixel value in the tomographic image 2, so if the calculated statistic exceeds the predetermined range, it is likely that the deformation and registration have been unsuccessful. In this case, the display image selection unit 46 determines that the tomographic image 2 is not an appropriate image to be displayed, and selects as a display image a notification image (or the combined image of the tomographic image 2 and the notification image) indicating that the tomographic image 2 is not an appropriate image to be displayed. On the other hand, if the statistic is within the predetermined range, the display image selection unit 46 selects a display image according to the method described in the above-described exemplary embodiment. In other words, the display image selection unit 46 selects one of the tomographic image 2, the notification image indicating that the distance between the cross-sectional positions of the tomographic images 1 and 2 is great, and the combined image of the tomographic image 2 and the notification image as a display image.

By the above-described processing, the notification image is displayed not only in the case where the distance between the tomographic images 1 and 2 is great but also in the case where the statistic of the tomographic image 2 exceeds the predetermined range (the case where it is likely that the deformation and registration have been unsuccessful). In this way, it is possible to prevent the user from referring to an inappropriate difference image despite the intention of the user to make a diagnosis from the current image.

Other Exemplary Embodiment

While the exemplary embodiments have been described in detail, the present invention can also be implemented as, for example, a system, apparatus, method, program, or recording medium (storage medium). Specifically, the present invention is also applicable to a system including a plurality of devices (e.g., host computer, interface device, image capturing device, web application) or an apparatus consisting of a single device.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-169608, filed Aug. 31, 2016, which is hereby incorporated by reference herein in its entirety.

What is claimed is:

1. An image display apparatus comprising:
a first acquisition unit configured to acquire a first tomographic image from a first three-dimensional image including a plurality of tomographic images;
a second acquisition unit configured to acquire a second tomographic image at a cross-sectional position corresponding to the first tomographic image from a processed image obtained by performing image processing on the first three-dimensional image and a second three-dimensional image;
a third acquisition unit configured to acquire a notification image for notifying that the second acquisition unit is unsuccessful in acquiring the second tomographic image or that a correspondence relationship between the first tomographic image and the second tomographic image does not satisfy a predetermined condition;
a selection unit configured to select the second tomographic image as a display image in a case where the second acquisition unit successfully acquires the second tomographic image or in a case where the correspondence relationship between the first tomographic image and the second tomographic image satisfies the predetermined condition, or select the notification image as a display image in a case where the second acquisition unit unsuccessfully acquires the second tomographic image or in a case where the correspondence relationship does not satisfy the predetermined condition; and
a display unit configured to display the first tomographic image and the display image selected by the selection unit in parallel or in a superimposed manner.

2. The image display apparatus according to claim 1, wherein the predetermined condition is a condition that a difference between a cross-sectional position of the first tomographic image and a cross-sectional position of the second tomographic image is smaller than or equal to a threshold value, and the selection unit selects the second tomographic image as a display image if the predetermined condition is satisfied, and the selection unit selects the notification image as a display image if the predetermined condition is not satisfied.

3. The image display apparatus according to claim 1, wherein the predetermined condition is a condition that a difference between a cross-sectional position of the first tomographic image and a cross-sectional position of the second tomographic image is smaller than or equal to a threshold value, and the selection unit selects the second tomographic image as a display image if the predetermined condition is satisfied, or the selection unit selects a combined image of the second tomographic image and the notification image as a display image if the predetermined condition is not satisfied.

4. The image display apparatus according to claim 3, wherein the selection unit sets, based on the difference, a combining ratio between the second tomographic image and the notification image in generating the combined image.

5. An image display method comprising:
acquiring a first tomographic image from a first three-dimensional image including a plurality of tomographic images;
acquiring a second tomographic image at a cross-sectional position corresponding to the first tomographic image from a processed image obtained by performing image processing on the first three-dimensional image and a second three-dimensional image;
acquiring a notification image for notifying that the second tomographic image is unsuccessfully acquired or that a correspondence relationship between the first tomographic image and the second tomographic image does not satisfy a predetermined condition;
selecting the second tomographic image as a display image in a case where the second tomographic image is successfully acquired or in a case where the correspondence relationship between the first tomographic image and the second tomographic image satisfies the predetermined condition, or selecting the notification image as a display image in a case where the second tomographic image is unsuccessfully acquired or in a case where the correspondence relationship does not satisfy the predetermined condition; and
displaying the first tomographic image and the selected display image in parallel or in a superimposed manner.

6. A non-transitory storage medium storing a program for causing a computer to execute:
acquiring a first tomographic image from a first three-dimensional image including a plurality of tomographic images;
acquiring a second tomographic image at a cross-sectional position corresponding to the first tomographic image from a processed image obtained by performing image processing on the first three-dimensional image and a second three-dimensional image;
acquiring a notification image for notifying that the second tomographic image is unsuccessfully acquired or that a correspondence relationship between the first tomographic image and the second tomographic image does not satisfy a predetermined condition;
selecting the second tomographic image as a display image in a case where the second tomographic image is successfully acquired or in a case where the correspondence relationship between the first tomographic image and the second tomographic image satisfies the predetermined condition, or selecting the notification image as a display image in a case where the second tomographic image is unsuccessfully acquired or in a case where the correspondence relationship does not satisfy the predetermined condition; and
displaying the first tomographic image and the selected display image such that the first tomographic image and the selected display image are displayed next to each other or superimposed.

7. An image processing apparatus, comprising:
a first acquisition unit configured to acquire a first tomographic image from a first three-dimensional image including a plurality of tomographic images;
a second acquisition unit configured to acquire a second tomographic image at a cross-sectional position corresponding to the first tomographic image from a processed image obtained by performing image processing on the first three-dimensional image and a second three-dimensional image;
a third acquisition unit configured to acquire a notification image for notifying that the second acquisition unit does not acquire the second tomographic image or that a correspondence relationship between the first tomographic image and the second tomographic image does not satisfy a predetermined condition;
a selection unit configured to select the second tomographic image as a display image in a case where the second acquisition unit successfully acquires the second tomographic image or in a case where the correspondence relationship between the first tomographic image and the second tomographic image satisfies the predetermined condition, or select the notification image as a display image in a case where the second acquisition unit does not acquire the second tomographic image or in a case where the correspondence relationship does not satisfy the predetermined condition; and
a display control unit configured to display, on a display screen, the first tomographic image and the display image selected by the selection unit in parallel or in a superimposed manner.

8. The image processing apparatus according to claim 7, wherein the predetermined condition is a condition that a difference between a cross-sectional position of the first tomographic image and a cross-sectional position of the second tomographic image is smaller than or equal to a threshold value, and the selection unit selects the second tomographic image as a display image if the predetermined condition is satisfied, and the selection unit selects the notification image as a display image if the predetermined condition is not satisfied.

9. The image processing apparatus according to claim 7, wherein the predetermined condition is a condition that a difference between a cross-sectional position of the first tomographic image and a cross-sectional position of the second tomographic image is smaller than or equal to a threshold value, and the selection unit selects the second tomographic image as a display image if the predetermined condition is satisfied, or the selection unit selects a combined image of the second tomographic image and the notification image as a display image if the predetermined condition is not satisfied.

10. The image processing apparatus according to claim 9, wherein the selection unit sets, based on the difference, a combining ratio between the second tomographic image and the notification image in generating the combined image.

* * * * *